United States Patent [19]
Lee

[11] Patent Number: 5,599,391
[45] Date of Patent: Feb. 4, 1997

[54] FINGERPRINTING DEVICE

[76] Inventor: Raymond Lee, 880 Boynton Ave., Apt. 13A, Bronx, N.Y. 10473

[21] Appl. No.: 529,327

[22] Filed: Sep. 18, 1995

[51] Int. Cl.[6] ........................................ B41K 1/00
[52] U.S. Cl. .................. 118/31.5; 118/264; 118/265; 118/266; 118/712; 427/1
[58] Field of Search .................... 118/31.5, 264, 118/265, 266, 712; 427/1

[56] References Cited

U.S. PATENT DOCUMENTS

| | | | |
|---|---|---|---|
| 2,232,783 | 2/1941 | Hausheer | 118/31.5 |
| 2,313,807 | 3/1943 | Curry | 427/1 |
| 3,694,240 | 9/1972 | Miller et al. | 118/31.5 |
| 3,830,195 | 8/1974 | Burleson | 118/31.5 |
| 4,404,926 | 9/1983 | McCormick-Goodhart et al. | 118/31.5 |

*Primary Examiner*—Donald E. Czaja
*Assistant Examiner*—Michael P. Colaianni

[57] ABSTRACT

A fingerprinting device including a hollow housing having a finger receiving entryway, a paper exit, and a charcoal-laden pad coupled thereto for receiving fingers of a user's hand thereupon; a press area coupled to the housing at a location offset below the finger receiving entryway for receiving charcoal-laden fingers of the user's hand thereupon; an axially-rotatable tubular roll of adhesive tape coupled to the housing and extended over the press area and through the paper exit and with charcoal from the user's fingers adhering to the tape to thereby create a negative print on the tape; an axially rotatable tubular roll of paper coupled to the housing and extended through the paper exit; and a pressurized roller mechanism for temporarily adhering the charcoal-laden tape with the paper and fixedly adhering the charcoal with the paper as the tape and paper travel toward the paper exit to thereby create a positive print on the paper and with the tape removable from contact with the paper to allow the positive print to be directly viewed in hard copy form.

6 Claims, 3 Drawing Sheets

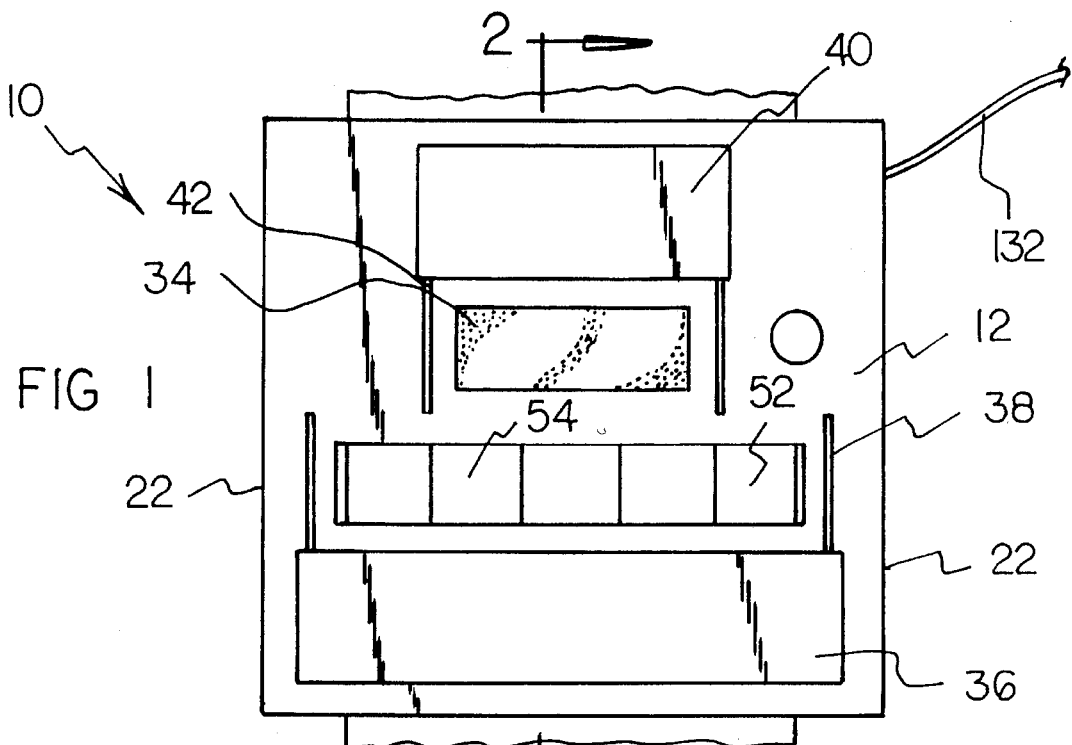
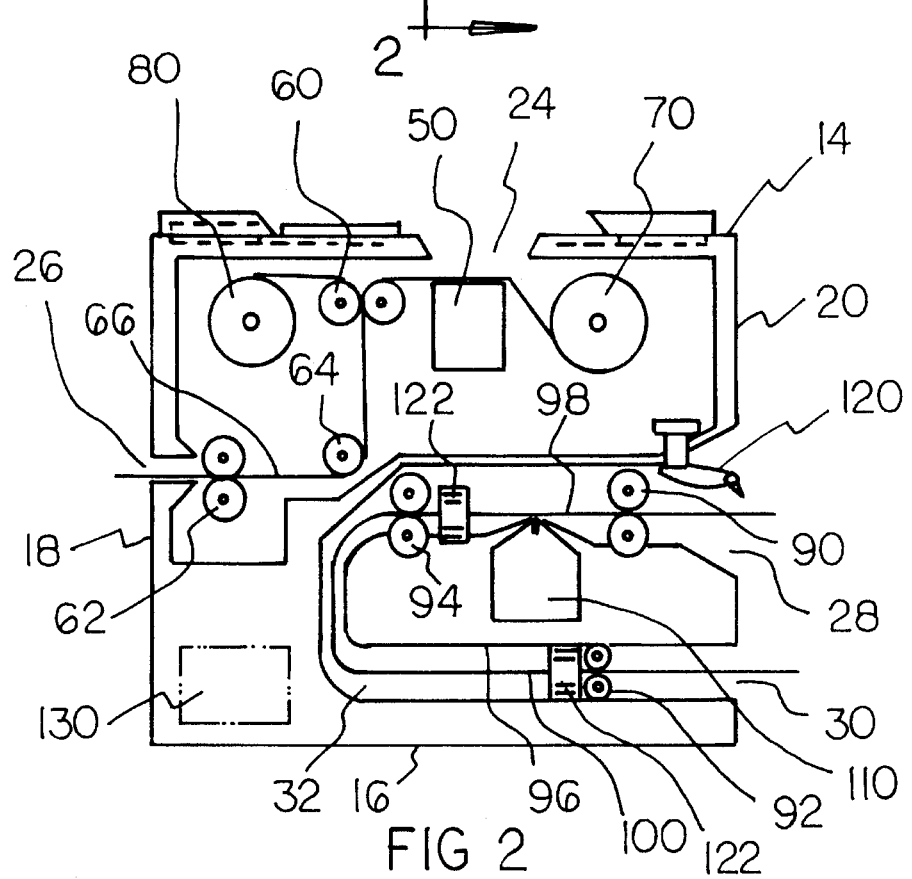

FINGERPRINTING DEVICE

BACKGROUND OF THE INVENTION

1. Field of the Invention

The present invention relates to a fingerprinting device and more particularly pertains to acquiring a user's fingerprints in a hard copy and a digital form with a fingerprinting device.

2. Description of the Prior Art

The use of fingerprinting apparatuses is known in the prior art. More specifically, fingerprinting apparatuses heretofore devised and utilized for the purpose of acquiring a user's fingerprints are known to consist basically of familiar, expected and obvious structural configurations, notwithstanding the myriad of designs encompassed by the crowded prior art which have been developed for the fulfillment of countless objectives and requirements. While the heretofore devised fingerprinting apparatuses fulfill their respective, particular objectives and requirements, none of the apparatuses provide a structure that allows a user's fingerprints to be readily obtained in a press-fit hard copy or a digital form.

In this respect, the fingerprinting device according to the present invention substantially departs from the conventional concepts and designs of the prior art, and in doing so provides an apparatus primarily developed for the purpose of acquiring a user's fingerprints in a hard copy and a digital form.

Therefore, it can be appreciated that there exists a continuing need for new and improved fingerprinting device which can be used for acquiring a user's fingerprints in a hard copy and a digital form. In this regard, the present invention substantially fulfills this need.

SUMMARY OF THE INVENTION

In the view of the foregoing disadvantages inherent in the known types of fingerprinting apparatuses now present in the prior art, the present invention provides an improved fingerprinting device. As such, the general purpose of the present invention, which will be described subsequently in greater detail, is to provide a new and improved fingerprinting device and method which has all the advantages of the prior art and none of the disadvantages.

To attain this, the present invention essentially comprises, in combination, a hollow and rigid housing having a top wall, a bottom wall, a front wall, a back wall, and two opposed side walls, a finger receiving entryway formed on the top wall, a first paper exit formed on the front wall, a paper entryway formed on the back wall, a second paper exit formed on the back wall between the paper entryway and the bottom wall, a channel extended between the paper entryway and the second paper exit, a charcoal-laden pad coupled to the top wall on one side of the finger receiving entryway and sized for receiving fingers of a user's hand thereupon for transferring charcoal thereto, a first door slidably coupled to the top wall and positionable over the finger receiving entryway for precluding access thereto, and a second door slidably coupled to the top wall and positionable over the pad for precluding access thereto. A box-shaped press area is included and coupled to the housing at a location offset directly below the finger receiving entryway. The press area has a top surface with a length of about 12 inches and a width of between about 2½ to 3 inches for receiving charcoal-laden fingers of the user's hand thereupon. A first pair of opposed and axially-rotatable pressure rollers are included and coupled to the housing between the press area and the front wall. A second pair of opposed and axially-rotatable pressure rollers are included and coupled to the housing near the first paper exit. An axially-rotatable guiding roller is included and coupled to the housing at a location offset from the first pair and the second pair of pressure rollers to create a generally L-shaped upper paper pathway. The upper paper pathway has an upper vertical portion extended from the first pair of pressure rollers to the guiding roller and a lower horizontal portion extended from the guiding roller to the second pair of pressure rollers and through the first paper exit.

An axially-rotatable tubular roll of clear adhesive tape is included and coupled to the housing at a location between the press area and the back wall. The tape is extended over the press area and along the upper paper pathway. Charcoal from the user's charcoal-laden fingers adheres to the tape when the user's fingers are pressed against the top surface of the press area to thereby create a negative print on the tape. An axially rotatable tubular roll of paper is included and coupled to the housing at a location between the press area and front wall. The paper is extended along the upper paper pathway. The first and the second pair of pressure rollers temporarily adhere the charcoal-laden tape with the paper and fixedly adhere the charcoal with the paper and as the tape and paper travel toward the first paper exit to thereby create a positive print on the paper. The tape is manually removable from contact with the paper to allow the positive print to be directly viewed in hard copy form.

A third pair of axially-rotatable pressure rollers is included and coupled to the housing near the second paper entryway. A fourth pair of axially-rotatable pressure rollers is included and coupled to the housing near the second paper exit. A fifth pair of axially-rotatable pressure rollers is included and coupled to the housing at a location offset from the third and the fourth pair of pressure rollers to define a generally U-shaped lower paper pathway. The lower paper pathway has an upper portion extended through the paper entryway and between the third and the fifth pair of pressure rollers and a lower portion extended between the fifth pair and the fourth pair of pressure rollers and through the lower paper exit. An electrically-energizable scanning means is provided. The scanning means is coupleable to an external computer. The scanning means is further coupled to the housing between the third and the fifth pair of pressure rollers at a location directly below the upper portion of the lower paper pathway. The scanning means is used for scanning the positive print in hard copy form to thereby create a positive print in digital form. An electrically-energizable sensor means is included for controlling flow of the positive print in hard copy form along the lower paper pathway and across the scanning means. An electrically-energizable drive means is included for axially rotating the rollers. Lastly, a power supply means is included and coupled to the scanning means, the sensor means, and the drive means for supplying electrical energy thereto for operation.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved fingerprinting device which has all the advantages of the prior art fingerprinting apparatuses and none of the disadvantages.

It is another object of the present invention to provide a new and improved fingerprinting device which may be easily and efficiently manufactured and marketed.

It is a further object of the present invention to provide a new and improved fingerprinting device which is of durable and reliable construction.

An even further object of the present invention is to provide a new and improved fingerprinting device which is susceptible of a low cost of manufacture with regard to both materials and labor, and which accordingly is then susceptible of low prices of sale to the consuming public, thereby making such a fingerprinting device economically available to the buying public.

Still yet another object of the present invention is to provide a new and improved fingerprinting device which provides in the apparatuses and methods of the prior art some of the advantages thereof, while simultaneously overcoming some of the disadvantages normally associated therewith.

Even still another object of the present invention is to provide a new and improved fingerprinting device for acquiring a user's fingerprints in a hard copy and a digital form.

Lastly, it is an object of the present invention to provide a new and improved fingerprinting device comprising a hollow housing having a finger receiving entryway, a paper exit, and a charcoal-laden pad coupled thereto for receiving fingers of a user's hand thereupon for transferring charcoal thereto; a press area coupled to the housing at a location offset below the finger receiving entryway for receiving charcoal-laden fingers of the user's hand thereupon; an axially-rotatable tubular roll of adhesive tape coupled to the housing and extended over the press area through the paper exit and with charcoal from the user's fingers adhering to the tape when the user's charcoal-laden fingers are pressed against the press area to thereby create a negative print on the tape; an axially rotatable tubular roll of paper coupled to the housing and extended through the paper exit; and pressurized roller means for temporarily adhering the charcoal-laden tape with the paper and fixedly adhering the charcoal with the paper as the tape and paper travel toward the paper exit to thereby create a positive print on the paper and with the tape removable from contact with the paper to allow the positive print to be directly viewed in hard copy form.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a plan view of the preferred embodiment constructed in accordance with the principles of the present invention.

FIG. 2 is a cross-sectional view of the present invention taken along the line 2—2 of FIG. 1.

The same reference numerals refer to the same parts through the various Figures.

DESCRIPTION OF THE PREFERRED EMBODIMENT

Figure 3:
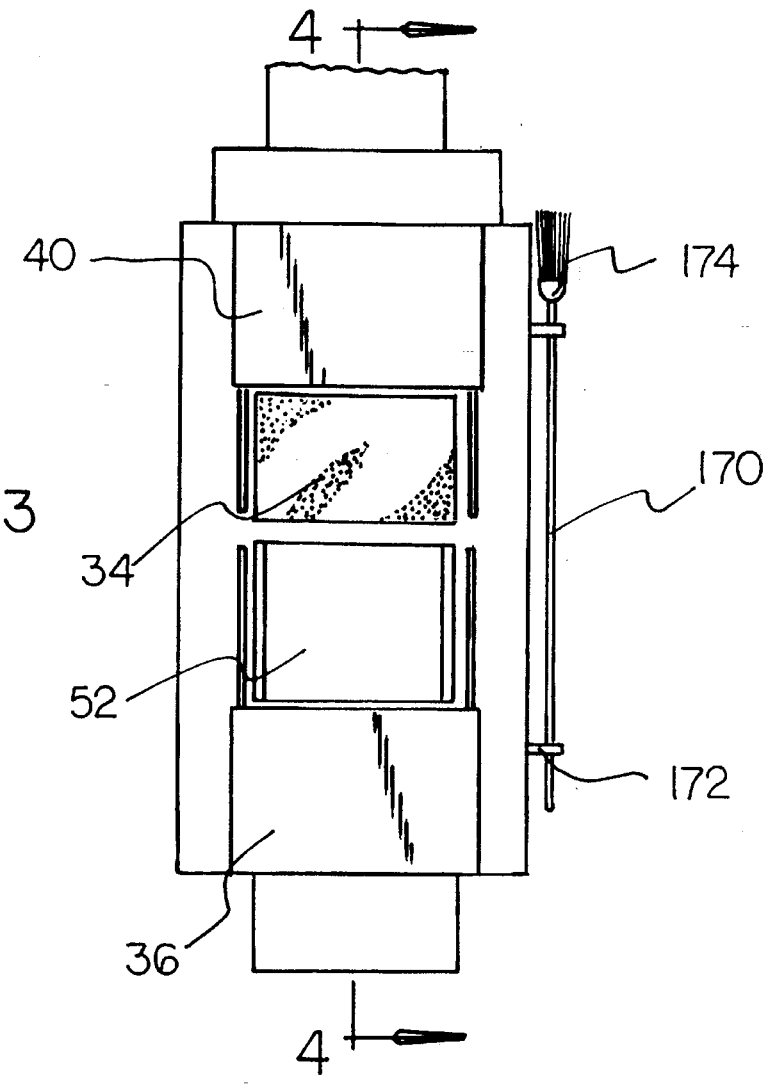
FIG. 3 is a plan view of an alternate embodiment of the present invention.

With reference now to the drawings, and in particular, to FIG. 1 thereof, the preferred embodiment of the new and improved fingerprinting device embodying the principles and concepts of the present invention and generally designated by the reference number 10 will be described.

The preferred embodiment of the present invention comprises a plurality of components. In their broadest context, such components include a housing, press area, rollers, adhesive tape, paper, a scanning mechanism, a sensor mechanism, a drive mechanism, and a power supply mechanism. Such components are individually configured and correlated with respect to each other to provide the intended function of acquiring a user's fingerprints in a hard copy form and a digital form.

Specifically, the present invention includes a free-standing housing 12. The housing is hollow and rigid in structure. The housing has a top wall 14, a bottom wall 16, a front wall 18, a back wall 20, and two opposed side walls 22. A generally rectangular finger receiving entryway 24 is formed on the top wall. A first paper exit 26 is formed on the front wall. A paper entryway 28 is formed on the back wall. A second paper exit 30 is formed on the back wall at a location between the paper entryway 28 and the bottom wall 16. A channel 32 is extended between the paper entryway and the second paper exit in a generally U-shaped configuration. In addition, a charcoal-laden rectangular pad 34 is coupled to the top wall 14 on one side of the finger receiving entryway 24. The charcoal of the pad can be of a block or of a dust form. The pad is sized for receiving fingers of a user's hand thereupon for transferring charcoal thereto. A first door 36 is slidably coupled to the top wall through use of a first pair of rails 38. The first door 36 is positionable over the finger receiving entryway 24 for precluding access thereto. Lastly, the housing includes a second door 40 slidably coupled to the top wall 14 with a second pair of rails 42. The second door is positionable over the pad 34 for precluding access thereto.

A box-shaped rigid press area 50 is coupled to the housing at a location offset directly below the finger receiving entryway 24 such as to form a baffle-type configuration. The press area has a planar top surface 52 with a length of about 12 inches and a width of about 2½ to 3 inches. The top surface of the press area 50 is used for receiving charcoal-laden fingers of a user's hand thereupon. The top surface 52 is further delineated by markers to thereby form five sequential spaces 54 for accommodating a user's thumb, an index finger, a middle finger, a second finger, and a little finger of the user's hand.

A first roller mechanism is provided. The roller mechanism is formed of a first pair 60 of opposed and axially rotatable pressure rollers. The first pair 60 of opposed and axially rotatable rollers are coupled to the housing between the press area 50 and the front wall 18. In addition, a second pair 62 of opposed and axially-rotatable pressure rollers are included. The second pair 62 of pressure rollers are coupled to the housing near the first paper exit 26. An axially rotatable guiding roller 64 is coupled to the housing at a location offset from the first pair 60 and the second pair 64 of pressure rollers. The first pair 60, second pair 62, and guiding roller 64 define a generally L-shaped upper paper pathway 66. The upper paper pathway has an upper vertical portion extended from the first pair 60 of pressure rollers to the guiding roller 64 and a lower horizontal portion extended from the guiding rollers 64 to the second pair of pressure rollers 62 and through the first paper exit 26.

Coupled to the housing 12 is an axially rotatable and tubular role of clear adhesive tape 70. The adhesive tape is positioned at a location between the press area 50 and the back wall 20. The tape is extended over the top surface 52 of the press area 50 and along the upper paper pathway 66. Charcoal from the user's charcoal-laden fingers adheres to the tape 70 when the user's fingers are pressed against the top surface 52 of the press area to thereby create a negative print on the tape.

In addition, an axially rotatable tubular role of white paper 80 is coupled to the housing 12 at a location between the press area 50 and the front wall 18. The paper is extended along the upper paper pathway 66. The first pair 60 and the second pair 62 of pressure rollers adhere the charcoal-laden tape 70 with the paper 80 as the tape and paper travel toward the first paper exit 26. The charcoal on the tape fixedly adheres to the paper to thereby create a positive print on the paper. The tape is manually removable from contact with the paper. The tape allows a portion of the charcoal to remain on the paper and thereby allow the positive print to be directly viewed in hard copy form. Both the roll of tape and roll of paper are replaceable through one or more access panels formed on the housing.

A second roller mechanism is also provided. The second roller mechanism includes a third pair of opposed and axially rotatable pressure rollers 90 coupled to the housing near the second paper entryway 28. In addition, a fourth pair of opposed and axially rotatable pressure rollers 92 are coupled to the housing near the second paper exit 30. A fifth pair of opposed and axially rotatable pressure rollers 44 are coupled to the housing at a location offset from the third pair 90 and the fourth pair 92 of pressure rollers to define a generally U-shaped lower paper pathway 96 aligned within the channel 32. The lower paper pathway has an upper portion 98 extended through the paper entryway 28 and between the third pair 90 and the fifth pair 94 of pressure rollers. The pathway also has a lower portion 100 extended between the fourth pair 92 and the fifth pair 94 of pressure rollers and through the lower paper exit 30.

An electrically-energizable scanning mechanism 110 is coupleable to an external computer through a line 112. The scanning mechanism is further coupled to the housing 12 between the third pair 90 and the fifth pair 94 of pressure rollers at a location directly below the upper portion 98 of the lower paper pathway 96. The scanning mechanism is used for scanning the positive print in hard copy form to thereby create a positive print in a digital form. The scanning mechanism has a window 114 positioned in juxtaposed relation with the paper along the lower paper pathway 96 to ensure that an accurate scan is obtained. The scanning mechanism is conventional in design and commercially available. Once the positive print of the fingerprint in digital form is obtained, it can be processed by the computer or sent by modem to another location.

An electrically-energizable sensor mechanism is used for controlling flow of the positive print in hard copy form along the lower paper pathway and across the scanning mechanism 110. The sensor mechanism includes a paper entry sensor arm 120 for detecting the presence of paper and two paper pathway position sensors 122 for allowing the control of the scanning speed of the paper across the window 114 of the scanner.

An electrically-energizable drive means 130 is also provided and engaged with the rollers through an actuation mechanism. The drive means allows the rollers to be axially rotated and is controlled through the sensor mechanism. The drive means manually activated and deactivated. A portion of the drive means is coupled to and controlled by sensors 120 and 122.

A power supply mechanism 132 is coupled to the scanning mechanism 110, the sensors 120, 122, and the drive mechanism 130. The power supply mechanism supplies electrical energy for operation. The power supply mechanism includes a power cable that has a plug affixed to a distal end thereof for securement with an external electrical receptacle.

Figure 4:
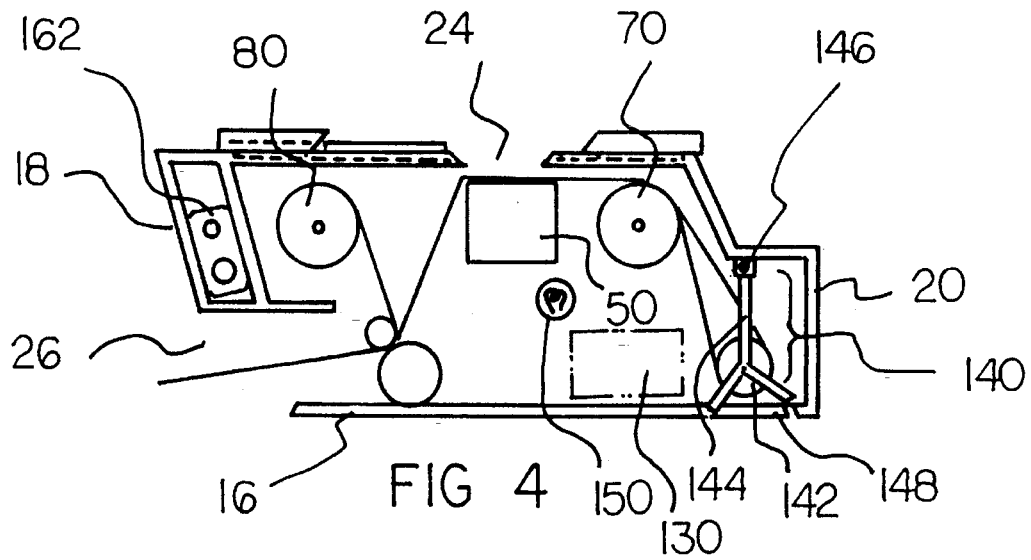
FIG. 4 is a cross-sectional view of an alternate embodiment of the present invention taken along the line 4—4 of FIG. 3.
Figure 5:
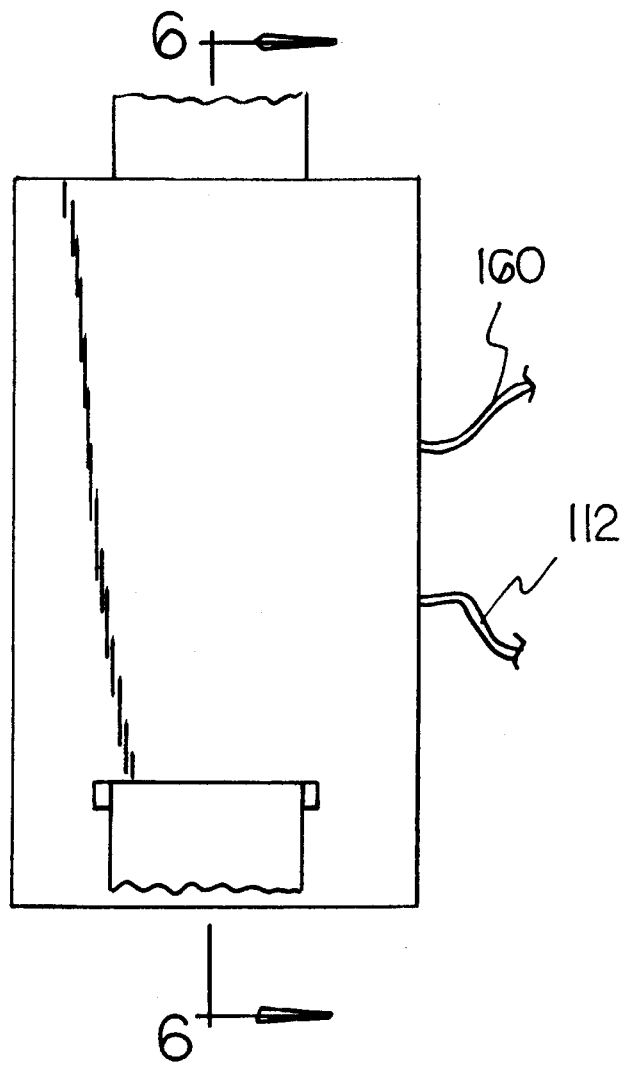
FIG. 5 is a view of an embodiment similar to that of FIG. 3, but with power lines to a cigarette lighter and to a modem.
Figure 6:
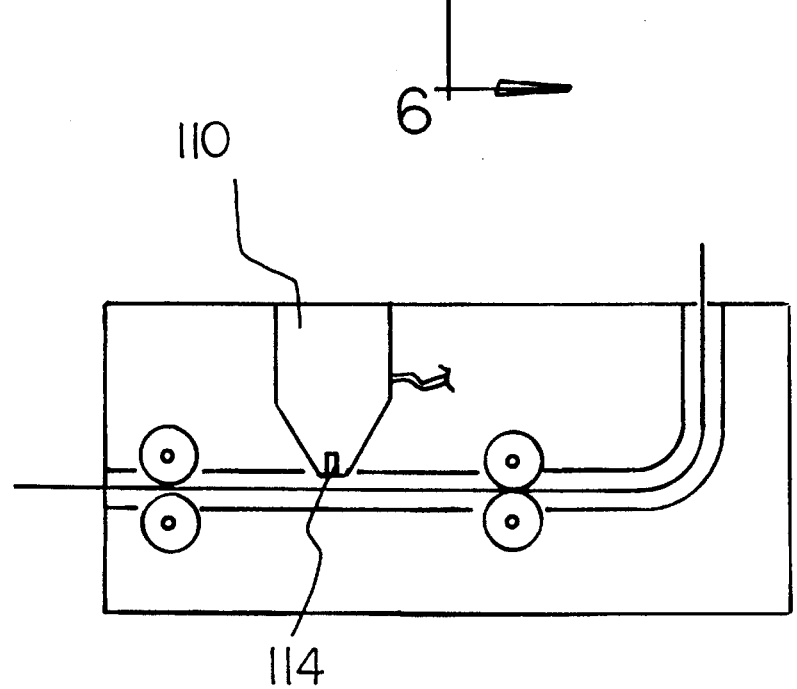
FIG. 6 is a cross-sectional view taken along lines 6—6 of FIG. 5.

A second embodiment of the present invention is shown in FIGS. 3–6. The second embodiment includes substantially all of the components of the present invention but is portable in design to allow its use in a motor vehicle. The second embodiment also includes a tensioning mechanism 140. The tensioning mechanism is used for maintaining a positive pressure upon the tape 70 so that it does not slip when a user's fingers are pressed thereupon and when the tape is positioned above the top surface 52 of the press area. The tensioning mechanism 140 includes a roller 142 engaged with the tape, a vertically positioned arm 144 coupled to the roller 142 and extended upwards therefrom, and an engagement mechanism actuated by a button 146 coupled between the arm 144 and the back wall 20 for allowing manual adjustment of the tensioning mechanism. In addition, a light bulb 150 is disposed within the housing and coupled with the power supply mechanism. The light bulb provides background illumination through the finger receiving entryway for facilitating the correct positioning of a user's fingers upon the top surface 52 of the press area. A door 148 is formed on a lower extent of the housing for allowing access to the tensioning mechanism 140. In the second embodiment, the power supply mechanism includes a power cable 160 with a plug that is coupleable to an external direct current power source such as a cigarette lighter socket of a motor vehicle for receiving electrical power therefrom in one mode of operation. Furthermore, a nine-volt is battery 162 secured within the housing for supplying electrical energy in another mode of operation. These modes of operation are controlled via a switching mechanism coupled between the power cable 160 and battery 162.

In addition, a third embodiment of the present invention includes substantially all of the components of the second embodiment and includes a scanner 110 for allowing scanning of the positive print in hard copy form to a positive print in digital form as previously described. Lastly, a brush 170 is removably attached to the housing 12 through use of fasteners 172. The brush 170 has a plurality of bristles 174 extended outwards therefrom. The brush is used for brushing charcoal off of the press area after use.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by LETTERS PATENT of the United States is as follows:

1. A fingerprinting device for acquiring a user's fingerprints in a hard copy form and a digital form comprising, in combination:

a hollow and rigid housing having a top wall, a bottom wall, a front wall, a back wall, and two opposed side walls, a finger receiving entryway formed on the top wall, a first paper exit formed on the front wall, a paper entryway formed on the back wall, a second paper exit formed on the back wall between the paper entryway and the bottom wall, a channel extended between the paper entryway and the second paper exit, a charcoal-laden pad coupled to the top wall on one side of the finger receiving entryway and sized for receiving fingers of a user's hand thereupon for transferring charcoal thereto, a first door slidably coupled to the top wall and positionable over the finger receiving entryway for precluding access thereto, and a second door slidably coupled to the top wall and positionable over the pad for precluding access thereto, a box-shaped press area coupled to the housing at a location offset directly below the finger receiving entryway and with the press area having a top surface with a length of about 12 inches and a width of between about 2½ to 3 inches for receiving charcoal-laden fingers of the user's hand thereupon;

a first pair of opposed and axially-rotatable pressure rollers coupled to the housing between the press area and the front wall;

a second pair of opposed and axially-rotatable pressure rollers coupled to the housing near the first paper exit;

an axially-rotatable guiding roller coupled to the housing at a location offset from the first pair and the second pair of pressure rollers to create a generally L-shaped upper paper pathway, and with the upper paper pathway having an upper vertical portion extended from the first pair of pressure rollers to the guiding roller and a lower horizontal portion extended from the guiding roller to the second pair of pressure rollers and through the first paper exit;

an axially-rotatable tubular roll of clear adhesive tape coupled to the housing at a location between the press area and the back wall with the tape extended over the press area and along the upper paper pathway and with charcoal from the user's charcoal-laden fingers adhering to the tape when the user's fingers are pressed against the top surface of the press area to thereby create a negative print on the tape;

an axially rotatable tubular roll of paper coupled to the housing at a location between the press area and front wall with the paper extended along the upper paper pathway and with the first and the second pair of pressure rollers temporarily adhering the charcoal-laden tape with the paper and fixedly adhering the charcoal with the paper as the tape and paper travel toward the first paper exit to thereby create a positive print on the paper, and with the tape manually removable from contact with the paper to allow the positive print to be directly viewed in hard copy form;

a third pair of axially-rotatable pressure rollers coupled to the housing near the second paper entryway;

a fourth pair of axially-rotatable pressure rollers coupled to the housing near the second paper exit;

a fifth pair of axially-rotatable pressure rollers coupled to the housing at a location offset from the third and the fourth pair of pressure rollers to define a generally U-shaped lower paper pathway and with the lower paper pathway having an upper portion extended through the paper entryway and between the third pair and the fifth pair of pressure rollers and a lower portion extended between the fifth pair and the fourth pair of pressure rollers and through the lower paper exit;

electrically-energizable scanning means couplable to an external computer and further coupled to the housing between the third and the fifth pair of pressure rollers at a location directly below the upper portion of the lower paper pathway for scanning the positive print in hard copy form to thereby create a positive print in digital form;

electrically-energizable sensor means for controlling flow of the positive print in hard copy form along the lower paper pathway and across the scanning means;

electrically-energizable drive means for axially rotating the rollers; and power supply means coupled to the scanning means, the sensor means, and the drive means for supplying electrical energy thereto for operation.

2. A fingerprinting device comprising:

a hollow housing having a finger receiving entryway, a paper exit, and a charcoal-laden pad coupled thereto for receiving fingers of a user's hand thereupon for transferring charcoal thereto;

a press area coupled to the housing at a location offset below the finger receiving entryway for receiving charcoal-laden fingers of the user's hand thereupon;

an axially-rotatable tubular roll of adhesive tape coupled to the housing and extended over the press area through the paper exit and with charcoal from the user's fingers adhering to the tape when the user's charcoal-laden fingers are pressed against the press area to thereby create a negative print on the tape;

an axially rotatable tubular roll of paper coupled to the housing and extended through the paper exit; and pressurized roller means for temporarily adhering the charcoal-laden tape with the paper and fixedly adhering the charcoal with the paper as the tape and paper travel toward the paper exit to thereby create a positive print on the paper and with the tape removable from contact with the paper to allow the positive print to be directly viewed in hard copy form.

3. The fingerprinting device as set forth in claim 2 and further including an electrically-energizable scanning means couplable to an external computer and further coupled to the housing for scanning the positive print in hard copy form to thereby create a positive print in digital form.

4. The fingerprinting device as set forth in claim 2 and further including electrically-energizable drive means for axially rotating the roller means.

5. The fingerprinting device as set forth in claim 2 and further including:

a first door coupled to the housing and positionable over the finger receiving entryway; and a first door coupled to the housing and positionable over the charcoal-laden pad.

6. The fingerprinting device as set forth in claim 2 and further including a brush removably attached to the housing and with the brush used for brushing charcoal off of the press area.

* * * * *